United States Patent
Niemeyer et al.

(10) Patent No.: US 10,730,071 B2
(45) Date of Patent: *Aug. 4, 2020

(54) METHOD FOR PRODUCING A PLURALITY OF MEASUREMENT REGIONS ON A CHIP, AND CHIP HAVING A PLURALITY OF MEASUREMENT REGIONS

(71) Applicant: Boehringer Ingelheim Vetmedica GmbH, Ingelheim am Rhein (DE)

(72) Inventors: Axel Niemeyer, Ingelheim am Rhein (DE); Heinz-Ulrich Schoeder, Ingelheim am Rhein (DE); Matthias Griessner, Ingelheim am Rhein (DE)

(73) Assignee: BOEHRINGER INGELHEIM VETMEDICA GMBH, Ingelheim am Rhein (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/367,518

(22) Filed: Dec. 2, 2016

(65) Prior Publication Data

US 2017/0157641 A1 Jun. 8, 2017

(30) Foreign Application Priority Data

Dec. 2, 2015 (DE) .......... 10 2015 120 935

(51) Int. Cl.
| | | |
|---|---|---|
| *B01L 3/00* | (2006.01) | |
| *B05D 3/06* | (2006.01) | |
| *B05D 1/00* | (2006.01) | |
| *B05D 1/28* | (2006.01) | |
| *G01N 33/543* | (2006.01) | |

(52) U.S. Cl.
CPC .............. *B05D 3/06* (2013.01); *B01L 3/5085* (2013.01); *B01L 3/5088* (2013.01); *B05D 1/005* (2013.01); *B05D 1/28* (2013.01); *G01N 33/54386* (2013.01); *B01L 2200/12* (2013.01); *B01L 2300/0819* (2013.01); *B01L 2300/0893* (2013.01); *B01L 2300/161* (2013.01)

(58) Field of Classification Search
CPC ............ B01L 3/5085; B01L 2300/089; B01L 2300/16; B01L 2300/161; B01L 3/5088
See application file for complete search history.

(56) References Cited

U.S. PATENT DOCUMENTS

| | | | |
|---|---|---|---|
| 4,231,660 A | * | 11/1980 | Remy .............. A61N 1/04 356/244 |
| 5,585,450 A | | 12/1996 | Oaks et al. |
| 5,985,551 A | | 11/1999 | Brennan |
| 6,020,110 A | | 2/2000 | Williams et al. |
| 6,183,970 B1 | | 2/2001 | Okano et al. |
| 6,210,894 B1 | | 4/2001 | Brennan |
| 6,734,436 B2 | | 5/2004 | Faris et al. |
| 6,779,637 B2 | | 8/2004 | Aoi et al. |

(Continued)

FOREIGN PATENT DOCUMENTS

| | | |
|---|---|---|
| JP | 2000297853 A | 10/2000 |
| WO | 2014/191114 A2 | 12/2014 |

*Primary Examiner* — Jill A Warden
*Assistant Examiner* — Dwayne K Handy
(74) *Attorney, Agent, or Firm* — David S. Safran; Roberts Calderon Safran & Cole, P.C.

(57) ABSTRACT

A method for producing a plurality of measurement regions on a chip, and a chip having a plurality of measurement regions which is obtainable by the method.

28 Claims, 3 Drawing Sheets

(56) References Cited

U.S. PATENT DOCUMENTS

| | | |
|---|---|---|
| 6,881,379 B1 | 4/2005 | Bredehorst et al. |
| 7,326,460 B2 | 2/2008 | Hirai |
| 7,399,585 B2 | 7/2008 | Gau |
| 2002/0119579 A1 | 8/2002 | Wagner |
| 2002/0123048 A1 | 9/2002 | Gau |
| 2002/0150506 A1 | 10/2002 | Okamoto et al. |
| 2003/0019704 A1 | 1/2003 | Aoi et al. |
| 2003/0047688 A1 | 3/2003 | Fads et al. |
| 2003/0194709 A1 | 10/2003 | Yang |
| 2004/0018615 A1* | 1/2004 | Garyantes ............ B01F 13/0071 435/305.2 |
| 2004/0055901 A1 | 3/2004 | Petersen et al. |
| 2004/0058423 A1 | 3/2004 | Albritton et al. |
| 2004/0146849 A1 | 7/2004 | Huang et al. |
| 2004/0224303 A1 | 11/2004 | Spencer et al. |
| 2004/0237590 A1 | 12/2004 | Sakoske et al. |
| 2004/0241742 A1 | 12/2004 | Peck et al. |
| 2004/0248122 A1 | 12/2004 | Martin et al. |
| 2004/0253545 A1* | 12/2004 | David ............... B01L 3/502707 430/311 |
| 2004/0258832 A1 | 12/2004 | Barklund et al. |
| 2005/0272268 A1 | 12/2005 | Hwang et al. |
| 2006/0110945 A1 | 5/2006 | Ho et al. |
| 2006/0159849 A1 | 7/2006 | Morita et al. |
| 2007/0207055 A1 | 9/2007 | Marchand et al. |
| 2009/0000957 A1 | 1/2009 | Dubin et al. |
| 2009/0131278 A1 | 5/2009 | Wagner et al. |
| 2009/0298191 A1 | 12/2009 | Whitesides et al. |
| 2011/0152124 A1 | 6/2011 | Baldi Coll et al. |
| 2011/0244639 A1 | 10/2011 | Ogawa et al. |
| 2016/0126151 A1 | 5/2016 | Schieber et al. |

\* cited by examiner

METHOD FOR PRODUCING A PLURALITY OF MEASUREMENT REGIONS ON A CHIP, AND CHIP HAVING A PLURALITY OF MEASUREMENT REGIONS

BACKGROUND OF THE INVENTION

Field of the Invention

The present invention relates to the technical field of microfluids, in particular to microfluids in combination with semiconductor technology. In particular, the present invention relates to a method for producing a plurality of measurement regions on a chip.

The present invention moreover relates to a chip having a multiplicity of electrically addressable measurement regions.

Description of Related Art

Microfluid systems are outstandingly suitable for carrying out chemical and biological detection reactions with low sample volumes.

In the field of clinical chemistry, in particular in biological and chemical diagnostics, chip-based systems, known as microarrays, are increasingly relied upon in particular in the detection of pathogens, such as, for example, viruses. Chip-based investigation methods allow simultaneous detection of a multiplicity of chemical or biological reactions in the smallest space. In this manner, on the one hand the requirement for cost-intensive laboratory equipment can be saved, and on the other hand a multiplicity of measurements can be carried out at the same time, so that even the results of complex investigations as a rule are available promptly.

Such chips which are suitable for chemical and biological investigation methods, in particular medical investigation methods, conventionally have a plurality of measurement regions, each of which is functionalized with different chemical or biological molecules so that different chemical reactions can take place and be detected in the individual measurement regions.

A chip having a multiplicity of measurement regions is known, for example, from U.S. Patent Application Publication 2009/0131278 A1. This is a silicon-based chip on the surface of which a multiplicity of electrode pairs is arranged by metallising and structuring. In each case, one electrode pair is present in a measurement region and the measurement regions are arranged in a chequered manner in one plane and form an array.

The electrode pairs each comprise microstructured finger electrodes intermeshed with one another, so that the electrodes in each case have adjacent interfaces over wide regions. The individual measurement regions are separated from one another by mechanical barriers in the form of small walls between the individual measurement regions, so that the measurement regions are present in the form of small compartments or cavities.

The individual measurement regions in such chips or microarrays are conventionally functionalized individually, in the context of chemical or biological diagnostics usually with biologically active substances. The biologically active substances can be, for example, antibodies which react chemically with specific antigens.

The chemical reaction can change the electrochemical relationships in the particular measurement region, so that the chemical reaction is detectable electrically by the electrode arrangement.

However, it is also possible that the molecules applied to the chip surface—capture molecules—react with specific target molecules, in particular bind these chemically, and the compound formed in this way is subsequently reacted chemically, this subsequent chemical reaction being detectable with the electrode arrangement.

The functionalizing is conventionally carried out by what is known as a spotting process, in which each measurement region is treated with a different solution or dispersion of a functionalizing reagent. Water is conventionally used as the solvent or dispersing agent for the functionalizing reagent, so that the measurement regions as a rule are formed hydrophilically, but at least are not hydrophobic.

The functionalizing reagent is immobilized on the chip surface by chemical reactions with the chip surface in the measurement regions or with the electrodes.

In order to obtain a result which is as unambiguous and reproducible as possible by using the chip, it is essential that the various liquids used during the spotting process are not mixed with one another, but each remain by themselves in the envisaged measurement region.

The mechanical barriers provided between the individual measurement regions in the above-mentioned U.S. Patent Application Publication 2009/0131278 A1 usually cannot prevent liquid from passing over from one measurement region into another, since due to the small extent of the individual measurement regions, which is in the micrometer range, and the relatively small width of the barrier between the individual measurement regions in combination with the high surface tension of the water, the liquids mix with one another.

In order to counteract this disadvantage, International Patent Application Publication WO 2014/191114 A2 proposes providing the regions between the individual measurement regions with a hydrophobic coating, in particular with a monolayer based on a perfluoroalkylsilane. Improved results in the spotting process can in fact be achieved in this manner, although the formation of a hydrophobic monolayer on the chip leads to problems in the actual measurement, especially if the chip has to be wetted over a large area with several reagents in succession for the detection. In particular, those reactions in which a substance, for example an antigen, is bound to the substrate, for example an antibody, bonded to the chip surface and the compound formed must then be reacted again for the detection are difficult to carry out with the system described. Individual separate vessels on the chip surface would be advantageous here, also because of the larger sample volume.

U.S. Pat. No. 6,779,637 B2 describes a system for producing hydrophilic measurement regions and hydrophobic intermediate regions, wherein in this case also the regions between the individual measurement regions are said to be raised as little as possible.

Highly hydrophilic measurement regions moreover have the disadvantage that, in particular with an otherwise hydrophobic chip surface, the spotting process can indeed be carried out very precisely and cleanly, but complete removal of individual reagent or sample solutions if the chip surface is wetted several times is possible only with difficulty.

Measurement methods are often sought in which a chip can be treated with several reagent or sample solutions, for example with different solutions of several amplification products for detection of a virus, wherein the specific antibodies present in different measurement regions each bind to particular antigens. Between each wetting of the chip with a solution containing amplification products the chip is cleaned such that all residues of the previous amplification product solution are removed from the chip surface. After the chip surface or the measurement regions have been wetted with the amplification product solutions, a developer solution which reacts with the particular compounds or conjugates in the measurement regions is then applied to the chip surface. This reaction can be detected by the electrodes. It is advantageous here for the chip and in particular the measurement regions to be covered such that the individual measurement regions form closed vessels. A particularly high reproducibility of the results is ensured in this way.

A chip would thus be desirable for which the fluid properties are developed such that on the one hand clean spotting of the individual measurement regions is possible, and on the other hand the chip can be wetted several times in sequence with different reagents, wherein the reagents in each case can be removed again without residue before wetting is carried out with a further reagent. Such properties depend not only on the material of the chip or of the measurement regions and of the mechanical barriers or coatings defining the measurement regions, but rather also on the concrete dimensions of the chip and of the measurement regions, in particular the depth and the diameter of the measurement regions and the spacing of the individual measurement regions.

The prior art thus lacks a concrete configuration of the measurement regions in combination with suitable materials in order to ensure not only defect-free spotting of the individual measurement regions but rather also an improved and reproducible measurement on the chip.

SUMMARY OF THE INVENTION

The present invention is thus based on the object of avoiding or at least reducing the disadvantages associated with the above-mentioned prior art.

A further object of the present invention is moreover to be seen in providing a method for producing a chip, and a corresponding chip which has improved fluid properties. In particular, an object of the present invention is to be seen in providing a chip which on the one hand can be functionalized selectively with the spotting process without problems, but on the other hand also allows wetting of the measurement regions with different reagents for the measurement and removal of these reagents from the measurement regions again without residue. The measurement region moreover should be configured such that it can accommodate a suitable amount of reagents, in particular reagent volumes or sample volumes, and can be closed.

The present invention according to a first aspect of the present invention thus provides a method for producing a plurality of measurement regions as described herein.

The present invention according to a second aspect of the present invention further provides a chip having a multiplicity of electrically addressable measurement regions as described herein.

It goes without saying that characteristics, features, configurations and embodiments as well as advantages or the like which are described in the following—for purposes of avoiding unnecessary repetitions—only for one aspect of the invention of course apply accordingly with respect to the other aspects of the invention without this having to be expressly mentioned.

It furthermore goes without saying that in the subsequent disclosure of values, numbers and ranges, the values, numbers and ranges stated in this respect are not to be understood as limiting; rather, it goes without saying for a person skilled in the art that the ranges or statements can be deviated from due to the individual case or in relation to the use without departing from the scope of the present invention.

Furthermore, all the stated values or parameters or the like mentioned in the following can in principle be ascertained or determined with normalized or standardized or explicitly mentioned determination methods or with determination methods which are familiar per se to a person skilled in the art in this field.

It moreover goes without saying that all weight-related or amount-related percentage data are selected by a person skilled in the art such that 100% results in total, which however goes without saying. On this basis, the present invention is described in more detail in the following.

The present invention—according to a first aspect of the present invention—thus provides a method for producing a plurality of measurement regions, in particular in the form of cavities, on a chip, wherein:

(a) in a first method step, a coating composition based on at least one organic polymer is applied to the chip surface;

(b) in a subsequent method step, the coating composition is cured at least in part and/or at least in some regions; and (c) in another subsequent method step, the coating composition is removed at least in some regions, so that individual measurement regions are defined and at least one three-dimensional hydrophobic structure, in particular a hydrophobic layer, is formed on the chip surface.

The three-dimensional hydrophobic structure or the three-dimensional hydrophobic layer in general forms a raised structure or layer on the chip surface. By the hydrophobic structure or hydrophobic layer on the one hand the individual measurement regions are defined, and on the other hand the individual measurement regions are separated from one another, in particular separated completely from one another, by the hydrophobic structure or hydrophobic layer. The hydrophobic structure preferably surrounds the individual measurement regions completely.

Cavities are thus preferably produced on the chip surface by the hydrophobic structure or the hydrophobic layer, in particular individual measurement vessels which can accommodate on the one hand the functionalizing solution for the spotting process and on the other hand the sample and reagent solution for the measurement methods.

In the context of the present invention, here a layer is to be understood as meaning any flat structure, in particular plane, which extends parallel to the two main directions of extension of the chip surface and the chemical composition of which differs from the surrounding material or which has interfaces perpendicular to the main direction of extension of the chip. In the context of the present invention, here a layer does not have to be continuous; rather it is possible for the layer to be interrupted or to comprise several individual regions on the chip surface. It is thus possible, for example, that the hydrophobic layer merely forms individual demarcations, in particular rings, around the measurement regions, this not being a preferred embodiment of the present invention.

In the context of the present invention, a hydrophobic structure or a hydrophobic layer is to be understood as meaning a structure or layer which has a contact angle to water of at least 60°.

In the context of the present invention, a curing of the coating composition in part is to be understood as meaning an incomplete chemical cross-linking of the molecules of the coating composition which form the hydrophobic structure or hydrophobic layer. In a curing of the coating composition in part some of the reactive chemical groups of the coating compositions are retained and can be cured completely, for example, in a later method step.

In the context of the present invention, curing of the coating composition in some regions is understood as meaning that individual, in particular locally demarcated, regions of the coating composition applied to the chip surface are cured, in particular cured at least in part, while other regions are not cured. Curing in some regions allows a very precise and less involved production of hydrophobic structures in only a few working steps, especially if photolithographic processes are used.

In the context of the present invention, a polymer is to be understood as meaning any at least dimeric compound which is formed by polymerisation or condensation and is obtainable from monomeric units. In the context of the present invention, the term polymer is understood as meaning in particular explicitly also oligomers, i.e. typically low molecular weight condensation or polymerisation products.

The method according to the invention allows a particularly simple production of measurement regions, in particular of measurement vessels in the form of cavities, on a chip surface.

In particular, by using photolithographic processes in which the coating composition is a photoresist, a precise structuring of the chip surface with a hydrophobic layer can be achieved in few working steps, wherein by the specific configuration of the layer geometry, i.e., inter alia the layer thickness, the spacing of the individual measurement regions and the diameter of the particular measurement regions, on the one hand a clean spotting, i.e., a defect-free functionalization of the individual measurement regions, is ensured, and on the other hand the measurement regions can be repeatedly wetted with sample or reagent solutions and then cleaned again, and in particular without artefacts for example in the form of cleaning liquid or undesirable reagent solution remaining in the individual measurement regions.

By producing cavities, in particular measurement vessels, on the chip surface it is moreover possible for the measurement regions not to have to have pronounced hydrophilic properties for carrying out the spotting process, which is conventionally carried out with aqueous solution. Since the walls of the measurement vessel formed by the hydrophobic structure in particular are hydrophobic, the spotting solution remains in the particular measurement region and the chip surface in the region of the measurement regions or the electrodes can be functionalized.

In the context of the present invention, the use of masks during application of the coating composition to the chip surface can in general be omitted. The use of masks during application of the coating composition has the decisive disadvantage that the mask has to be removed again after coating has been carried out. This leads either to the measurement regions losing contour sharpness in the case of non-cured coating composition, or to parts of the coating composition remaining adhered to the mask if the coating composition has cured at least in part, and in this way to the measurement region being damaged when the mask is removed.

The use of masks moreover also presents problems from the point of view that the surface properties of the coating composition or of the coating change at the interface of the mask to the coating composition, i.e. the resulting coating will have either a higher layer thickness in the interface region or a lower one than in regions further away, which in turn can adversely impair the overall performance of the chip.

In the context of the present invention, the chip surface is conventionally formed by a layer of silicon dioxide or silicon nitride, in particular silicon nitride. Surfaces of silicon dioxide allow the functionalization of the chip surface after prior activation by silanol groups, while silicon nitride is distinguished by a high passivation and in particular renders possible the use of gold electrodes. Silicon nitride moreover is far less hydrophilic than silicon dioxide and is therefore suitable in particular for chip systems which are treated with several sample or reagent solutions. Gold has an outstanding electrical conductivity and potentials which can be readily determined, and renders possible the bonding of chemical and biological compounds, for example via stable sulphur bridges, but has the disadvantage that it dopes silicon easily. As a result of this, the semiconductor properties of the chip, which in addition to the measurement region often contains microstructured electronic units for evaluation of the measurements, can be adversely influenced.

In the context of the present invention, the chips conventionally have electrode pairs. In particular, the measurement regions may be electrically addressable. Preferably, the measurement regions are electrically addressable such that electrically contactable electrodes are provided in the measurement regions.

As regards the removal of the coating composition in method step (c), this can be carried out in various ways. In general, the coating composition is removed in a locally selective manner in method step (c). In the context of the present invention, the coating composition is thus removed in a locally demarcated manner.

In particular, in the context of the present invention the measurement regions are exposed, i.e. the coating composition is removed in the region of the electrodes, so that measurement regions, in particular measurement vessels, having dimensions which can be determined precisely are defined.

Particularly preferably, in the context of the present invention here the coating composition is removed in method step (c) in a locally selective manner such that only the measurement regions are defined or created and the remainder of the chip surface remains covered with the hydrophobic structure, in particular the hydrophobic coating. In this manner, it is possible to avoid adhesion of excess reagent solution, which is conventionally formed in an aqueous manner, to the chip surface and to achieve a complete replacement of various sample and reagent solutions on the chip surface in the case of complex measurement methods.

The coating composition in method step (c) can be cured either in part or in some regions or completely, i.e., the coating composition can already have its final chemical structure in method step (c).

All measures known in the prior art are suitable for removing the coating composition, in particular it is possible to remove the coating by treatment with plasma, dry etching or by a wet chemical route with solvents or oxidising chemicals.

In the context of the present invention, it is preferable for the coating composition to be applied to the chip surface in the form of a layer, i.e., with a layer thickness which is as homogeneous as possible.

As regards the layer thickness with which the coating composition is applied to the chip surface, this can vary over a wide range. However, it has proved appropriate if the coating composition is applied to the chip surface with a layer thickness in the range of from 1 to 20 µm, in particular 2 to 15 µm, preferably 3 to 10 µm, more preferably 4 to 7 µm. Application of the coating composition with the abovementioned layer thicknesses results, after removal of any solvent or dispersing agent or after the curing operation, in hydrophobic structures or hydrophobic layers having layer thicknesses which on the one hand are outstandingly suitable for the spotting process and provide sufficiently large volumes for measurement in closed measurement systems, and on the other hand allow a quick and complete replacement of various sample, cleaning and reagent solutions.

In order to ensure a processing of the chip surface which is as simple as possible, the coating composition is preferably applied to the chip surface in particular at least substantially over the complete surface. This saves the adverse and involved use of mask systems when applying the coating composition, which as a rule require a likewise very involved reprocessing of the resulting coating. In particular, the use of mask systems presents problems in the demarcating of the measurement regions in a defined manner and the exact control of the properties of the coating at the interface between the coating composition and mask material.

As regards the application of the coating composition, this can likewise be carried out in various ways. However, it has proved appropriate if the coating composition is applied to the chip surface by means of pouring, knife-coating, rolling, spin-coating, in particular by means of spin-coating. In particular, the use of the spin-coating processes allows the layer thickness to be established in a very simple manner via the viscosity or flow properties of the coating composition and the speed of rotation.

In the context of the present invention, the coating composition is conventionally thermally cured and/or by means of radiation. Particularly good results are obtained in the context of the present invention if the coating composition is thermally cured and by means of radiation. Thermal curing or curing by means of radiation can be carried out in this context in working or method steps one after the other. It is thus possible, for example, by means of a photolithographic process that a part of the coating is first cured by means of radiation, the non-cured part of the coating is removed and the coating composition is then completely cured thermally.

In the context of the present invention, here, a thermal curing is to be understood as meaning that the coating composition cross-links by increasing the temperature. In the context of the present invention, curing by means of radiation, on the other hand, is to be understood as meaning a photochemical cross-linking reaction. Photochemical reactions take place under the action of electromagnetic radiation, wherein UV radiation is preferably employed in the context of the present invention.

In the context of the present invention, the coating composition is conventionally liquid. In this manner, a particularly uniform application of the coating composition with a homogeneous layer thickness can be achieved.

In particular, particularly good results are obtained if the coating composition has a Brookfield viscosity at 20° C. in the range of from 20 to 5,000 mPas, in particular 30 to 2,000 mPas, preferably 50 to 1,000 mPas, more preferably 100 to 500 mPas, particularly preferably 150 to 400 mPas. Coating compositions having the above-mentioned viscosities can be applied in thin layers without problems and form homogeneous layers.

As regards the composition of the coating composition used according to the invention, all suitable compositions can be used here. In particular, the coating composition employed according to the invention can be used in the form of an all-solid composition, i.e., a composition which has a solids content of 100 wt. % or almost 100 wt. % and manages without or with extremely small amounts of volatile organic solvents.

It is moreover also possible that the coating composition is formed on the basis of a solution or dispersion. In the context of the present invention, particularly good results are obtained if the coating composition is a solution or dispersion of the at least one organic polymer. The reason for this is in particular that the polymers preferably employed according to the invention can be readily handled in solutions or dispersions. In the context of the present invention, it is particularly preferable for the coating composition to be both an all-solid composition and a solution or dispersion of the at least one polymer.

The coating composition conventionally comprises at least one solvent or dispersing agent. Here in particular, the solvent or dispersing agent can be selected from aliphatic hydrocarbons, aromatic hydrocarbons, ethers, alcohols, aldehydes, ketones and nitriles and mixtures thereof, in particular aromatic hydrocarbons.

Particularly good results are obtained in the context of the present invention if the solvent or dispersing agent is selected from benzene, toluene, trimethylbenzenes, xylene and 2-methoxyethanol and mixtures thereof. Preferably, 1,3,5-trimethylbenzene is used as the solvent or dispersing agent. 1,3,5-Trimethylbenzene is largely inert under the conditions of use, i.e. in particular towards thermal or photochemical excitation, and can be removed simply by increasing the temperature or evaporation.

According to a particular embodiment of the present invention, the solvent or dispersing agent reacts, in particular reacts completely, with further constituents of the coating composition. The solvent or dispersing agent then becomes part of the hydrophobic structure. By this means the involved recovery of organic solvents is avoided, which is advantageous on the one hand in terms of environmental aspects and also from the point of view of a simplified process procedure.

As regards the amount of solvent or dispersing agent in the coating composition employed according to the invention, this can vary over a wide range. However, it has proved appropriate if the coating composition comprises the solvent or dispersing agent in amounts of from 10 to 90 wt. %, in particular 15 to 80 wt. %, preferably 20 to 70 wt. %, more preferably 30 to 60 wt. %, based on the coating composition. Solutions or dispersions with the above-mentioned weight contents of solvent or dispersing agent in general have viscosities which are advantageous for carrying out the method according to the invention.

The choice of polymer which is used for the coating composition employed according to the invention depends of course on the planned intended use of the chip. However, the polymer is conventionally obtainable by polymerisation or polycondensation from acrylic acid, methacrylic acid, esters of acrylic acid with $C_1$- to $C_6$-alcohols, esters of methacrylic acid with $C_1$- to $C_6$-alcohols, styrene, cyclobutarenes and mixtures thereof. Particularly good results are obtained in the context of the present invention if the polymer is obtainable by polymerisation of cyclobutarenes. In this connection, particularly good results are obtained if the polymer is obtainable from monomers of the group of

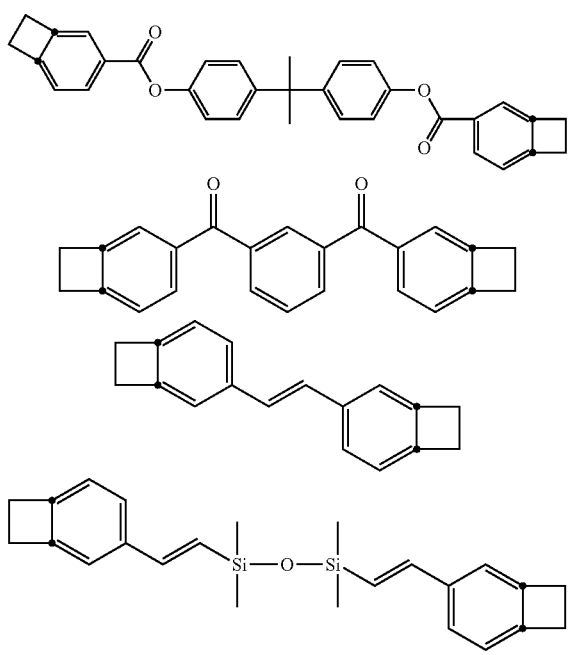

Particularly good results are obtained in the context of the present invention if the polymer is obtainable from divinyltetramethyldisiloxane-bis(benzocyclobutane). Such polymers are often also called BCB polymers and are marketed, for example, by The Dow Chemical Company under the trade name Cylotene®.

The processing properties, in particular the viscosity, of the coating compositions employed according to the invention depend to a high degree on the molecular weights of the polymers employed. In the context of the present invention, it has proved appropriate if the polymer has a weight-average molecular weight $M_w$ in the range of from 800 to 15,000 g/mol, in particular 900 to 10,000 g/mol, preferably 1,000 to 7,000 g/mol, more preferably 1,000 to 5,000 g/mol.

Likewise, the polymer can have a number-average molecular weight $M_n$ in the range of from 1,000 to 100,000 g/mol, in particular 5,000 to 90,000 g/mol, preferably 10,000 to 85,000 g/mol, more preferably 20,000 to 80,000 g/mol.

In the context of the present invention, the molecular weights are preferably determined by gel permeation chromatography (GPC).

The polymers preferably employed in the context of the present invention thus have a high polydispersity ($M_w/M_n$), which means that the polymers employed according to the invention have a wide bandwidth of various molecular weights. Due to the high polydispersity, a low viscosity of the coating composition can be established, by which means the coating composition can be cured rapidly.

The amount of polymer in the coating composition can likewise vary over a wide range. However, in order on the one hand to be able to establish the viscosity of the coating composition in an appropriate range and on the other hand to achieve coatings having an adequate layer thickness, it has proved appropriate if the coating composition comprises the polymer in amounts of from 5 to 80 wt. %, in particular 10 to 75 wt. %, preferably 15 to 70 wt. %, more preferably 25 to 55 wt. %, based on the coating composition.

As already described above, it is possible that the method according to the invention, in particular the production of the hydrophobic structure or the hydrophobic layer on the chip surface, is carried out by means of photolithographic processes. In the context of the present invention, it is even preferable for the method according to the invention to be carried out in the form of a photolithographic process, since in this manner on the one hand a high precision can be achieved in the removal of the coating composition in some regions, and on the other hand only a few working steps are necessary to achieve the desired result.

If the method according to the invention is carried out as a photolithographic process, the coating composition employed according to the invention is preferably a photoresist. If photolithographic process techniques are used or in the case of coating compositions which can be cured by radiation, it has proved appropriate if the coating composition comprises at least one photoinitiator.

In the case where the coating composition comprises a photoinitiator, the coating composition conventionally comprises the photoinitiator in amounts of from 0.01 to 10 wt. %, in particular 0.1 to 8 wt. %, preferably 0.5 to 7 wt. %, more preferably 1 to 5 wt. %, based on the coating composition. The above-mentioned amounts of photoinitiator allow a very rapid and homogeneous curing of the coating composition employed according to the invention by means of radiation.

As regards the chemical nature of the photoinitiator, all suitable compounds are likewise possible here. However, in the context of the present invention, it has proved appropriate if the photoinitiator is selected from azides, acrylates, acetylene, bismaleimides, isocyanates, conjugated aromatic ketones and benzophenones and mixtures thereof. Particularly good results are obtained if the photoinitiator is selected from azides.

In this connection it has proved appropriate if the photoinitiator is selected from 2,6-bis[3-(4-azidophenyl)-2-propenylidene]cyclohexanone, 2,6-bis[3-(4-azidophenyl)-2-propenylidene]-4-methylcyclohexanone, 2,6-bis(4-azidobenzal)-4-methylcyclohexanone, p-azidophenyl sulphone, m-azidophenyl sulphone, 4,4'-diazidostilbene, 4,4'-diazidobenzalacetophenone, 2,3-diazido-1,4-naphthoquinone, 4,4'-diazidodiphenylmethane and mixtures thereof.

According to a preferred embodiment of the present invention, the photoinitiator is 2,6-bis[3-(4-azidophenyl)-2-propenylidene]cyclohexanone.

In the context of the present invention, the coating composition can moreover comprise further additional substances, in particular at least one additive. If the coating composition comprises additives, the additives are in general selected from antioxidants, photosensitisers, rheology adjusters, stabilisers, preservatives and mixtures thereof. Preferably, the coating composition comprises at least an antioxidant and—in the case where the coating composition can be cured by radiation—a photoinitiator or mixtures thereof.

In the context of the present invention, it has proved appropriate if antioxidants based on phenol, sulphide, phosphite and amine compounds are employed, sterically hindered amines in particular deliver the best results. In particular, the use of sterically hindered amines having aliphatic and aromatic groups is preferred. Particularly good results are obtained in the context of the present invention if the antioxidant is polymerised 1,2-dihydro-2,2,4-trimethylquinoline.

It has moreover proved appropriate in the context of the present invention if 3,3'-carbonyl-bis(7-methoxycoumarin) or 3,3'-carbonyl-bis(7-diethylaminocoumarin) or mixtures thereof are used as photosensitisers.

If the coating composition employed according to the invention comprises an additive, the coating composition conventionally comprises the additive in amounts of from 0.01 to 10 wt. %, in particular 0.1 to 9 wt. %, preferably 0.2 to 8 wt. %, more preferably 0.5 to 7 wt. %, based on the coating composition.

In the context of the present invention, it is possible that after the application of the coating composition in method step (a) and before the curing of the coating composition in method step (b) the coating composition is subjected to a thermal treatment. The thermal treatment of the coating composition serves to remove readily volatile solvents and homogenise the layer applied to the chip surface, in particular strains between the individual polymer molecules are said to be broken down. By removal of the solvent in particular, the viscosity and therefore the structural stability of the coating composition are moreover increased.

If a thermal treatment of the coating composition is carried out, the coating composition is conventionally heated to temperatures in the range of from 40 to 150° C., in particular 50 to 140° C., preferably 60 to 130° C., more preferably 80 to 120° C. during the thermal treatment. The temperatures are preferably chosen such that no thermal curing process of the coating composition takes place yet.

As regards the duration of the thermal treatment of the coating composition before the curing operation, this can vary over a wide range depending on the particular requirements. However, it has been found that very good results are obtained if the coating composition is subjected to the thermal treatment for a duration of from 20 seconds to 10 minutes, in particular 30 seconds to 5 minutes, preferably 50 seconds to 3 minutes, more preferably 60 seconds to 120 seconds.

According to a particular embodiment of the present invention, the coating composition is thermally cured in method step (b), in particular thermally cured over the complete surface.

In this connection, it has proved appropriate in particular if the coating composition is also cured completely, i.e. not cured only in part. Since a thermal curing can be carried out in a locally selective manner only with difficulty, the method according to the invention according to this specific embodiment is carried out such that the complete layer is thermally cured, in particular also completely thermally cured. If the coating composition is thermally cured in method step (b), it has proved appropriate if the coating composition is cured at temperatures in the range of from 100 to 350° C., in particular 150 to 320° C., preferably 180 to 300° C., more preferably 200 to 280° C.

As regards the period of time in which the coating composition is thermally cured, this can vary within a wide range. The longer the coating composition is cured, the higher the percentage of reacted reactive groups. It has been found that good results can be obtained if the coating composition is cured in a period of time of from 10 minutes to 20 hours, in particular 20 minutes to 5 hours, preferably 30 to 120 minutes, more preferably 40 to 90 minutes.

If the coating composition is thermally cured, in particular in method step (b), particularly good results are obtained if the coating composition is subjected to a heating program, in particular a multistage heating program, before the actual curing process. By the heating program, in particular by multistage heating of the coating composition to the curing temperature, it is ensured that the coating composition is heated homogeneously and cures uniformly. The coating composition moreover can also expand uniformly, as a result of which the homogeneity of the resulting coating is increased. A heating program by way of example can be configured as follows: Heating to 100° C. over the course of 15 minutes, holding the temperature at 100° C. for a further 15 minutes, heating to 150° C. over the course of 15 minutes, holding the temperature at 150° C. for 15 minutes and increasing the temperature to the curing temperature over the course of 60 minutes.

If the coating composition is thermally cured in method step (b), the cured coating composition is removed at least in some regions in method step (c). Plasma processes, such as dry etching, in which in particular mixtures of oxygen and a fluorine-containing gas, such as, for example, carbon tetrafluoride, hexafluoroethane, perfluoroisobutene, sulphur hexafluoride and nitrogen trifluoride, are suitable in particular here. Particularly good results are obtained if mixtures of oxygen and carbon tetrafluoride in a volume ratio of 4:1 or oxygen and sulphur hexafluoride in a volume ratio of 5:1 are used. With the aid of the etching techniques the measurement regions are exposed, masks which cover the regions to be obtained being used to protect the regions of the coating which are to be retained on the chip surface.

In this manner, in the context of the present invention high-performance hydrophobic coating systems can likewise be obtained on silicon-based chips, although the removal of the cured coating composition is significantly more involved than the removal of the non-cured coating composition, which is carried out, for example, in the case of photolithographic processes.

According to a preferred embodiment of the present invention, the coating composition is therefore cured, in particular cured in some regions, by means of radiation in method step (b). In the context of the present invention, it is preferable for the coating composition to be present as a photoresist. In this case it is possible to produce the hydrophobic structure or hydrophobic coating on the chip surface by photolithographic processes. Curing, in particular curing in some regions, of the coating composition in method step (b) is conventionally carried out here by UV radiation.

If the coating composition is cured by means of radiation in method step (b), it has proved appropriate if the coating composition is cured using a mask. In particular, a photomask is laid over the coated chip surface, and the coating composition is irradiated, those regions of the coating composition which are covered by the mask not being exposed to the radiation.

The use of a photomask allows in particular a locally selective curing of the coating by radiation. In the case of radiation curing, it can be that either the regions of the coating composition which are exposed to the radiation cure—negative photoresist—or the coating composition in total cures, for example by the action of moisture from the atmosphere, and those regions which are irradiated do not cure, for example by destruction of bonds within the polymer—positive photoresist. In the context of the present invention, it is preferable for the coating composition to be a negative photoresist, i.e. the regions of the coating composition which are exposed to the radiation cure.

It is moreover likewise possible that the coating composition is cured in part by the radiation. In this case a final thermal curing, for example after removal of the non-cured regions, is often carried out. This additional working step has the advantage that the layer is homogenised again by the thermal curing, since during the radiation curing the instantaneous actual state is preserved and as it were "frozen".

If the method according to the invention is carried out as a photolithographic process, the non-cured regions of the coating composition are conventionally removed.

In this connection, it has proved appropriate that the coating composition is removed chemically, in particular by treatment with at least one solvent. The removal of the non-cured regions by solvent is particularly easy and not very involved to carry out, so that by this means time and costs can be saved, very good results with respect to contour sharpness of the remaining coating being achieved at the same time. The removal of non-cured regions with a solvent is also called developing in photolithographic processes.

As regards the choice of solvent for removing the non-cured regions of the coating composition, particularly good results are obtained if the solvent is selected from the group of xylene, 1,3,5-trimethylbenzene, benzene, toluene, 2-methoxydimethyl ether, dipropylene glycol dimethyl ether, N-methylpyrrolidone, butyric acid n-butyl ester and lactic acid ethyl ester and mixtures thereof. Preferably, the solvent is butyric acid n-butyl ester.

According to this embodiment of the present invention, the coating composition can moreover be thermally cured in a subsequent method step (d). In particular, the coating composition which has cured at least in part and remains on the chip surface after the removal of the coating composition in some regions is thermally cured. This has the advantage in particular that—as already stated above—the coating composition is homogenised again and stresses within the coating composition are broken down. Residues of readily volatile solvents which, for example, have been included in the layer during the radiation curing and do not react with the polymer can also escape again during the thermal curing. It is moreover also often not possible to obtain a resistance of the coating to chemical substances and UV radiation, such as is desired for the end use, by the radiation curing.

If the coating composition according to this embodiment is thermally cured, the coating composition is conventionally cured at temperatures in the range of from 100 to 350° C., in particular 150 to 320° C., preferably 180 to 300° C., more preferably 200 to 280° C.

If the coating composition is cured not only by radiation but subsequently also thermally, the coating composition is conventionally thermally cured in a period of time of from 10 minutes to 20 hours, in particular 20 minutes to 5 hours, preferably 30 to 120 minutes, more preferably 40 to 90 minutes. By this thermal curing operation the hydrophobic structure or hydrophobic layer on the chip surface formed from the coating composition acquires its final properties.

According to this embodiment also, in the context of the thermal curing it is preferable for the coating composition to be subjected to a multistage heating program. Since the coating or the coating composition is already pre-cured by radiation, the heating can be carried out faster than in the case of purely thermal curing. It is thus possible for example that the coating composition is heated to 150° C. over the course of 15 minutes, the temperature is kept at 150° C. for 15 minutes and heating to the curing temperature is then carried out.

According to this particular and preferred embodiment of the present invention, it is likewise possible that the coating is subjected to a thermal treatment after the curing of the coating composition in method step (b) and before the removal in some regions of the coating composition in method step (c). In this thermal treatment step, volatile solvent residues are again to be removed from the coating composition and the layer homogenised in order to obtain an improved hydrophobic structure or hydrophobic layer. However, in this connection it is also important that in this thermal treatment the coating composition is not thermally cured. The thermal treatment is optionally carried out in addition to the thermal treatment optionally carried out between method step (a) and (b).

If the coating composition is subjected to a thermal treatment, in particular a further thermal treatment, the coating composition is conventionally heated to temperatures in the range of from 30 to 100° C., in particular 40 to 80° C., preferably 50 to 70° C. The duration of the heating here is in general 0.5 to 20 minutes, in particular 1 to 10 minutes, preferably 3 to 6 minutes.

In the context of the present invention, the coated chip surface, i.e. the chip surface provided with a hydrophobic structure or hydrophobic layer, can moreover be subjected to a cleaning in a final method step (e).

Preferably, the cleaning in method step (e) is carried out by means of etching processes, in particular by means of dry etching. The above-mentioned process conditions and reagents are suitable in particular for dry etching, in particular combinations of oxygen and carbon tetrafluoride as well as oxygen and sulphur hexafluoride are preferred.

In the context of the present invention, the chip surface moreover is conventionally cleaned before application of the coating composition. The cleaning is conventionally carried out chemically, for example by treatment with oxidising cleaning solutions, such as, for example, a piranha solution, i.e. mixtures of sulphuric acid and hydrogen peroxide, or mixture of aqueous ammonia and hydrogen peroxide, and/or by treatment with organic solvents.

In order to improve the adhesion of the hydrophobic structure or the hydrophobic layer to the chip surface, in the context of the present invention an adhesion promoter can be applied to the chip surface before application of the coating composition.

If an adhesion promoter is used, the adhesion promoter is applied to the chip surface as uniformly and in as thin a layer as possible.

In the context of the present invention, it has proved appropriate if the adhesion promoter is at least a silane and/or comprises a silane. In this connection, it has proved appropriate if the silane is selected from the group of trialkoxyvinylsilanes, trialkoxyvinylsilylbenzocyclobutanes and trialkoxyaminosilanes and mixtures thereof. Particularly good results are obtained if the silane is selected from the group of 3-aminopropyltriethoxysilane, trimethoxyvinylsilane, triethoxyvinylsilane, trimethoxyvinylbenzocyclobutane, triethoxyvinylbenzocyclobutane and mixtures thereof. It is particularly preferable for the silane to be 3-aminopropyltriethoxysilane.

According to a particularly preferred embodiment of the present invention, the method according to the invention is a method for producing a plurality of measurement regions, in particular in the form of cavities, on a chip, in particular as described above, wherein in successive method steps
(i) where appropriate the chip surface is cleaned,
(ii) an adhesion promoter is applied to the chip surface,
(iii) a coating composition based on at least one organic polymer is subsequently applied to the chip surface,
(iv) the coating composition is subsequently subjected, where appropriate, to a first thermal treatment,
(v) the coating composition is cured at least in part and/or at least in some regions,
(vi) the coating composition is subjected, where appropriate, to a further thermal treatment,
(vii) the coating composition is subsequently removed at least in some regions, so that individual measurement regions are defined and at least one three-dimensional hydrophobic structure is formed on the chip surface, (viii) the coating composition is thermally cured, and
(ix) the coated chip surface is cleaned, in particular the measurement regions are cleaned.

Method step (iii) corresponds to method step (a) in the above statements. Method step (v) corresponds to method step (b) in the above statements, while method step (vii) corresponds to method step (c) in the above statements. Method step (viii) corresponds to method step (d) and method step (ix) corresponds to method step (e) in the above statements.

The method according to the invention is carried out in particular such that the cured coating has a layer thickness of from 0.5 to 20 µm, in particular 1 to 10 µm, preferably 2 to 8 µm, more preferably 3 to 7 µm, particularly preferably 4 to 6 µm. It is particularly preferable for the cured coating to have a layer thickness of 5 µm.

A layer thickness of the hydrophobic structure or the hydrophobic layer in the abovementioned ranges, in particular of 5 µm, as a rule allows the introduction of sufficiently large volumes of sample and/or reagent solution into the individual measurement regions and moreover renders possible a rapid and complete emptying of the individual measurement regions and the refilling with further solutions.

DETAILED DESCRIPTION OF THE INVENTION

Figure 1:
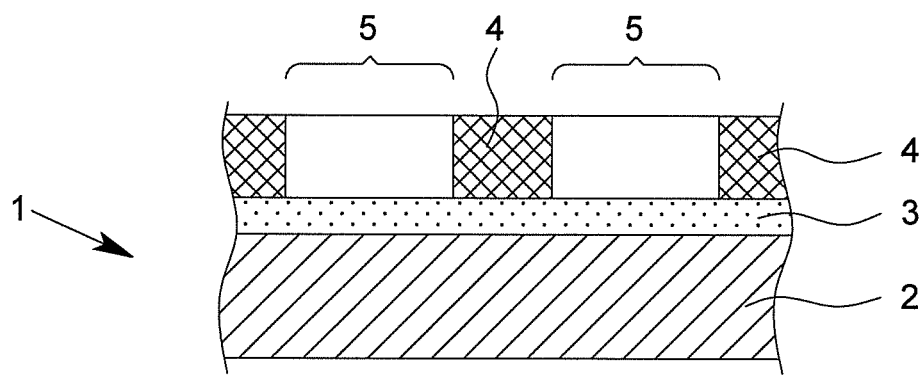
FIG. 1 is a side view of the chip according to the invention obtainable by the method according to the invention.

The present invention—according to a second aspect of the present invention—further provides a chip having a multiplicity of electrically addressable measurement regions, wherein a hydrophobic structure, in particular a hydrophobic layer, defining the measurement regions is provided on the chip surface, wherein the hydrophobic structure (4) is formed three-dimensionally.

In the context of the present invention, it is preferable for the chip surface to be formed at least substantially flat and for the hydrophobic structure to be raised relative to this. The hydrophobic structure or the hydrophobic layer is thus preferably a raised structure or layer.

Chips of particular performance are obtained in the context of the present invention if the hydrophobic structure has a layer thickness of from 0.5 to 20 µm, in particular 1 to 10 µm, preferably 2 to 8 µm, more preferably 3 to 7 µm, particularly preferably 4 to 6 µm. In the context of the present invention, it is preferable in particular for the hydrophobic structure to have a layer thickness of 5 µm. With layer thicknesses in the above-mentioned ranges—as already stated above—on the one hand an unambiguous and defect-free functionalizing of the individual measurement regions by the spotting process can be ensured, and on the other hand sufficiently large volumes of reagents can be filled into the measurement regions and also be removed again without residue, so that the chip can be wetted several times in succession with various sample or reagent solutions without problems.

In the context of the present invention, the hydrophobic structure conventionally not only defines the measurement regions, but rather also separates them from one another. In particular, it is preferable for the measurement regions to be surrounded completely by the hydrophobic structure, for example in a ring-like manner. It is equally preferable for the regions between the individual measurement regions to be covered with the hydrophobic structure, since in this manner undesirable accumulations of reagents, which are conventionally water-based, are avoided.

In general, in the context of the present invention the hydrophobic structure is formed in a grid-like and/or honeycombed manner. The hydrophobic layer thus preferably forms a sub-division on the chip, so that the measurement regions, in particular measurement vessels, are in each case formed over the electrode pairs. The individual measurement regions here preferably have a circular base area.

According to a preferred embodiment of the present invention, the hydrophobic layer forms hydrophobic regions between the measurement regions. In this connection it is preferable in particular for the hydrophobic regions between the measurement regions to have a width of more than 10%, in particular more than 20%, of the diameter of a measurement region. In this manner it is ensured that, during the spotting process in particular, mixing of the functionalizing reagents is avoided.

In the context of the present invention, it has equally proved advantageous for the hydrophobic regions between the measurement regions to have a width of more than 5 µm, in particular more than 10 µm, in particular more than 20 µm, particularly preferably more than 50 µm.

In order to avoid mixing of the functionalizing reagents during the spotting, it has proved appropriate if the ratio of the height of the hydrophobic structure to the width of the hydrophobic structure in the regions between the measurement regions is at least 1:5, in particular 1:8, preferably 1:10.

Likewise, the ratio of the height of the hydrophobic structure to the width of the hydrophobic structure in the regions between the measurement regions can be in the range of from 1:5 to 1:100, in particular 1:8 to 1:50, preferably 1:10 to 1:20.

The hydrophobic layer conventionally has a contact angle to water in the range of from 60 to 180°, in particular 70 to 150°, preferably 80 to 100°.

The hydrophobic layer—as already stated above—is conventionally formed on the basis of an organic polymer.

According to a preferred embodiment, the hydrophobic layer is formed on the basis of a photoresist. In particular, the coating composition employed for producing the coating is preferably a photoresist or contains a photoresist.

In the context of the present invention, the measurement regions can moreover have a diameter of from 50 to 500 µm, in particular 70 to 400 µm, preferably 90 to 300 µm, more preferably 100 to 250 µm, particularly preferably 120 to 180

μm. These diameters of the preferably circular measurement regions in combination with the layer thickness of the hydrophobic layer on the one hand make available a sufficiently large volume for carrying out and detecting the chemical reactions, but on the other hand render possible a quick and complete replacement of various reaction solutions.

As regards the volume of the measurement regions, in particular the measurement vessels, this can vary within wide ranges depending on the chemical and biological detection reactions carried out in each case. However, it has proved appropriate if the measurement regions have a volume of from 0.2 to 500 pl, in particular 0.5 to 300 pl, preferably 1 to 150 pl, more preferably 5 to 100 pl, particularly preferably 10 to 50 pl.

In the context of the present invention, it is moreover preferable for the hydrophobic layer to be chemically and/or physically stable at least in the short term at temperatures of up to 250° C., in particular up to 300° C., preferably up to 350° C. The hydrophobic layer should thus be stable at least when temperature peaks occur, such as may occur, for example, during sawing of a wafer into individual chips.

In the context of the present invention, the chip is in general obtainable or produced by the method according to the invention.

For further details on this aspect of the invention, reference may be made to the previous statements on the method according to the invention, which apply accordingly with respect to the chip according to the invention.

The subject matter of the present invention is explained in the following with the aid of preferred embodiments in the drawings, but without limiting this to the embodiments shown. Further modifications and characteristics of the method according to the invention and of the chip according to the invention are clear to the person skilled in the art on reading the description and the following description of the drawings.

FIG. 1 is a sectional view of a chip 1 according to the invention which is constructed from a substrate 2, in particular elemental silicon, on which a surface layer 3 is arranged. The surface layer 3 is preferably made of silicon dioxide or silicon nitride, the use of silicon nitride being preferred since silicon nitride prevents the diffusion of metal atoms, in particular of gold atoms, which is preferably used for the electrodes of the measurement regions, into the substrate 2.

On the surface layer 3 there is arranged a hydrophobic structure in the form of a hydrophobic layer 4, which defines and demarcates the measurement regions 5 by recesses. The ratio of the height of the hydrophobic layer 4 and the diameter of the preferably circular measurement regions 5 is chosen such that on the one hand a simple and defect-free spotting, i.e. a functionalizing of the measurement regions with chemical molecules, is possible, but on the other hand a faster and more complete replacement of reagents in the measurement regions is possible.

Figure 2:
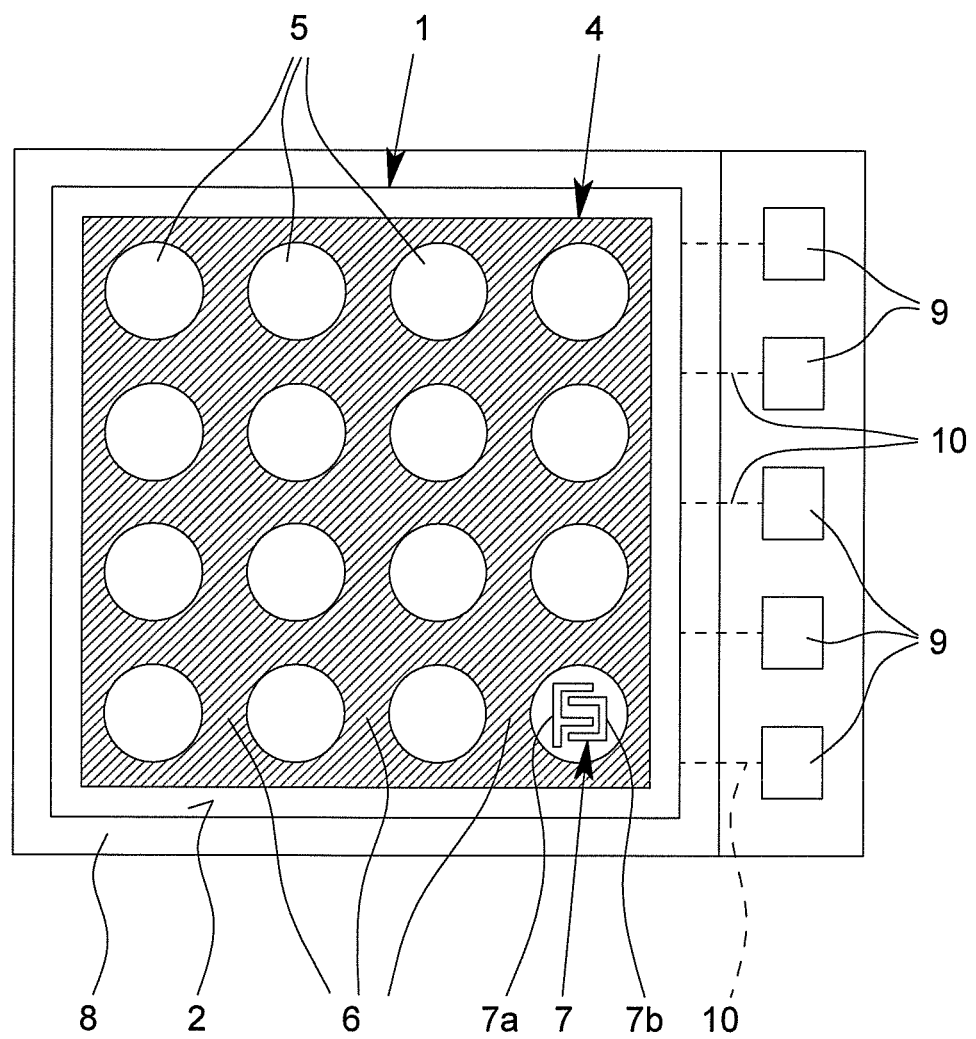
FIG. 2 is a simplified plan view of the chip according to the invention in the installed state.

FIG. 2 is a plan view of a simplified schematic drawing of the chip 1 according to the invention in the installed state. The hydrophobic layer 4 defines the individual measurement regions 5 and creates hydrophobic regions 6 between the measurement regions.

In the measurement regions there are arranged electrode pairs 7, which comprise finger electrodes 7A and 7B closely intermeshed with one another. The hydrophobic layer 4 forms a chequered or grid-like pattern, in particular a compartment structure, on the chip surface.

The chip is connected to or installed in a housing 8. Preferably, the chip 1 is produced together with other chips 1 in a conventional process, for example by the CMOS technique, on a common carrier or substrate, in particular a wafer. The chips 1 are then separated from one another, connected electrically and preferably installed, in particular in an assigned housing 8 or the like.

According to the drawing, the chip 1 is preferably connected electrically to contact surfaces or terminals 9, in particular via the electrical connections 10 indicated by broken lines, as shown in a highly schematic drawing. The electrical connection of the chip 1 is conventionally called bonding.

In the installed state at least the measurement regions 5 are accessible for accommodation of samples to be measured, which are not shown in the drawing.

In FIG. 2 an electrode arrangement 7 is shown schematically only in one measurement region 5. In particular, such preferably identical or similar electrode arrangements 7 are formed or arranged in all the measurement regions 5. The formation of the electrode arrangement 7 is preferably carried out before production or application of the hydrophobic layer 4. The electrode arrangements 7 preferably lie substantially in the chip surface 3, on which the measurement regions 5 are formed and the hydrophobic layer 4 is constructed.

In the embodiment shown, the hydrophobic layer 4 is continuous in formation, in particular the hydrophobic intermediate regions 6 between the individual measurement regions 5. However, it is also possible, although less preferable, that the hydrophobic layer 4 between the individual measurement regions 5 is not continuous, or is interrupted. Thus, for example, the individual measurement regions 5 can be merely surrounded by the hydrophobic structure 4 in a ring-like manner.

The individual measurement regions 5 preferably have a width or an average diameter of more than 50 μm, in particular more than 100 μm. The measurement regions 5 moreover can have a width or an average diameter of less than 500 μm, in particular less than 300 μm, preferably less than 200 μm. It is particularly preferable in this connection for the measurement regions to have a diameter of from 120 to 180 μm.

The electrode pairs 7A and 7B are preferably made of gold and are vapour-deposited on the chip surface 3 with the aid of mask technologies.

The measurement regions 5 are functionalized with the aid of a spotting process such that a drop of liquid (not shown in the drawing) having a volume of from 1 to 500 pl is introduced into the measurement regions 5. The drop of liquid comprises a functionalizing reagent which reacts either with the chip surface 3 in the measurement regions or with the electrodes 7A and 7B in the measurement regions 5 such that a chemical bond forms between the chip surface 3 or the electrodes 7 and the functionalizing reagent.

Due to the hydrophobic layer 4 and in particular intermediate regions 6, it is possible that the drops of liquid remain localised in the particular measurement regions 5 and do not mix with adjacent drops of liquid or flow into adjacent measurement regions 5. The spotting can in principle be carried out optionally before or after separation of the chip 1 and/or electrical connection and installation of the particular chip. The spotting is preferably carried out after connection and installation of the chip 1.

The measurement method with the functionalized measurement regions 5 is carried out in a manner in which a sample liquid (not shown in the drawing) or, in chronological sequence, several sample liquids with molecules to be detected or detecting molecules is or are introduced into the measurement regions 5. This can be carried out, for example, by wetting the entire chip surface and treatment with cleaning liquids. In particular, the chip, in particular the compartment structure, can be covered with a membrane for the actual measurement. The membrane here can interact with the compartment structure, in particular lie on this, in order to distribute the sample liquid over the measurement regions 5 and/or to achieve a fluid separation of the sample liquid in the various measurement regions 5 from one another.

Alternatively, however, it is also possible to apply one or more samples to be measured to the already functionalized measurement regions 5 by spotting, but this is significantly more involved.

Figure 3:
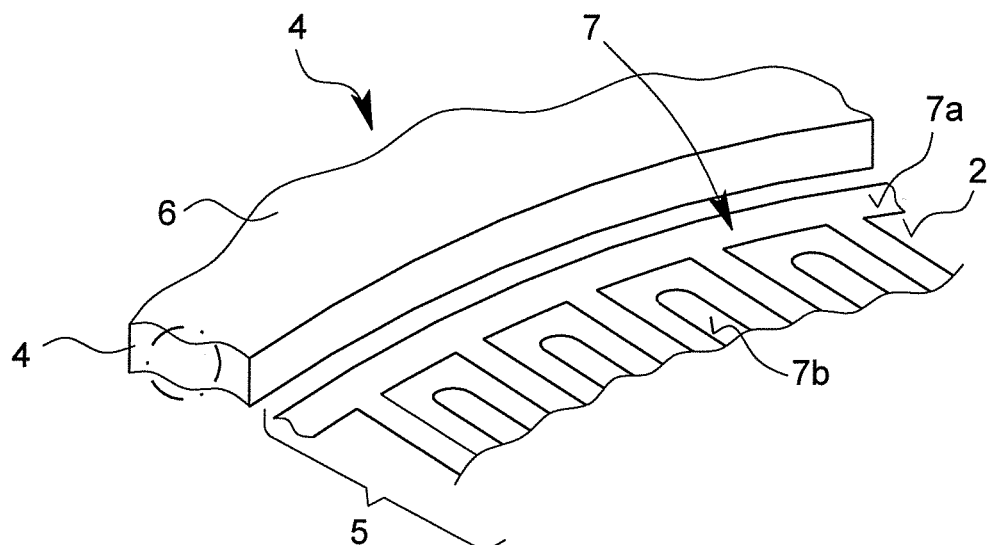
FIG. 3 is an enlarged perspective view of the edge region of a measurement region.

FIG. 3 in turn is an enlarged view of the edge region of a measurement region 5. In particular, in the drawing the chip surface 3 is preferably covered over the largest possible surface by the electrode pairs 7A and 7B and a measurement vessel is formed over the base area of the measurement regions 5 by the hydrophobic layer 4.

Figure 4:
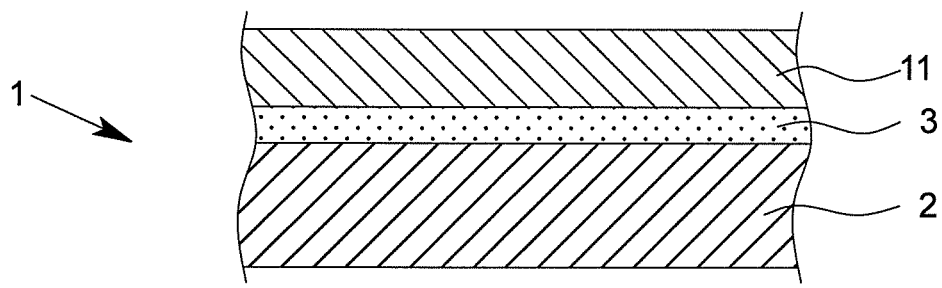
FIG. 4 shows a part step of the method according to the invention in which the chip surface is provided with a coating composition.

As can be seen from FIG. 4, in the context of the present invention to produce the chip 1 according to the invention a procedure is followed in which a coating composition 11 is applied to the chip surface 3, in particular is applied as homogeneously as possible and with a uniform layer thickness.

Figure 5:
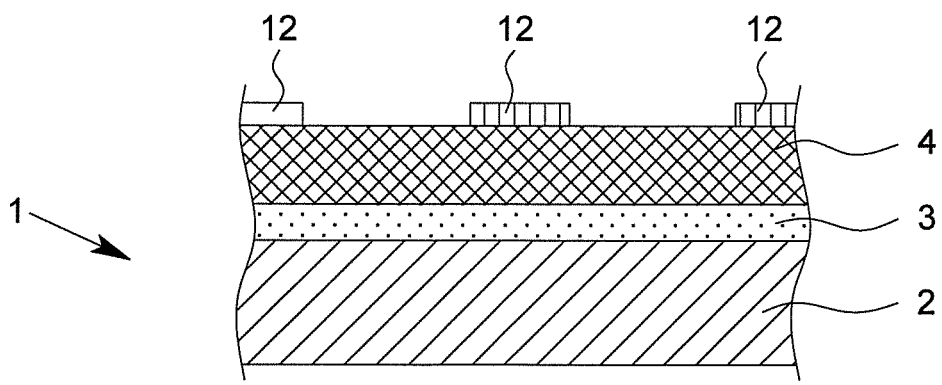
FIG. 5 shows an embodiment of the method according to the invention in which a mask is applied to the cured coating composition.

FIG. 5 shows an embodiment of the present invention in which the coating composition 11 has been thermally cured, so that the hydrophobic layer 4 forms, but still has no recess for the measurement regions. In order to expose the measurement regions 5, a mask 12 is applied to the hydrophobic layer 4, which covers the regions of the hydrophobic layer 4 which are not to be removed. The regions of the hydrophobic layer 4 which are not covered by the mask 12 are then removed preferably by dry etching, in particular by mixtures of oxygen and carbon tetrafluoride or oxygen and sulphur hexafluoride in a plasma. The mask here can be either a soft mask, which is attacked by the etching reagent, or a hard mask, which is inert with respect to the etching reagent.

Figure 6:
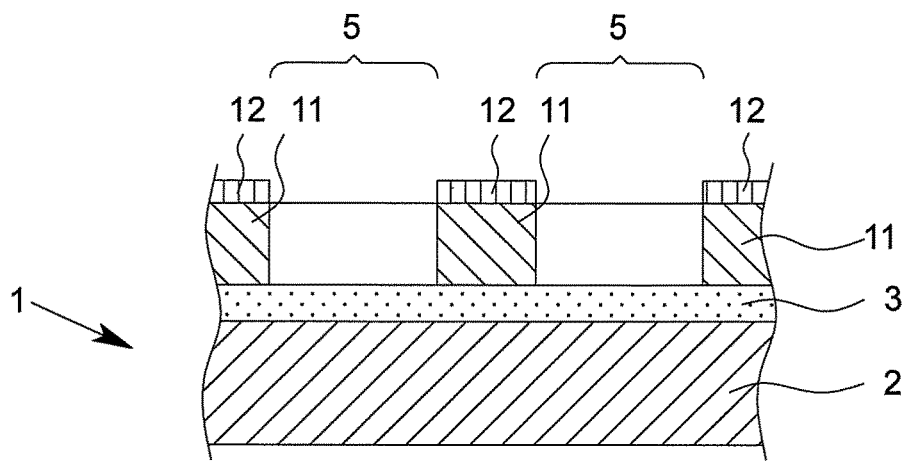
FIG. 6 shows a part step of the method according to the invention according to a particular embodiment in which the coating composition between the mask has been removed.

FIG. 6 schematically shows the chip 1 according to the invention on which the measurement regions 5 have been exposed by the etching process. After the etching process has been carried out, the mask 12 is removed again and the chip 1 according to the invention can be used after optionally further cleaning steps, in particular the measurement regions 5 can be functionalized with the aid of a spotting process.

Figure 7:
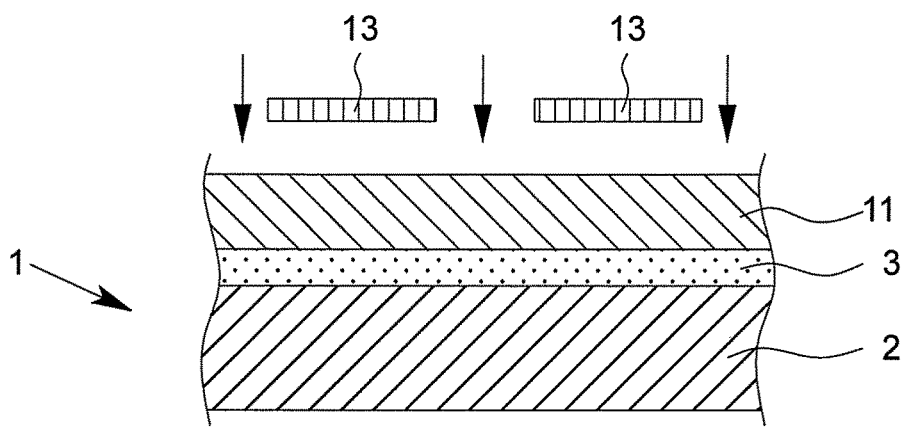
FIG. 7 shows an alternative and preferred embodiment of the method according to the invention, in which regions of the coating composition are exposed to light through a photomask.

FIG. 7 shows an embodiment which is preferred according to the invention, in which the hydrophobic layer 4 is produced by a photolithographic process. Here also, as with the exclusively thermal curing, a coating composition 11 is first applied to the chip surface 3. The coating composition 11 is then irradiated by UV radiation through a photomask 13. By this means, the regions of the coating composition 11 which are exposed to the UV radiation are preferably cured.

Figure 8:
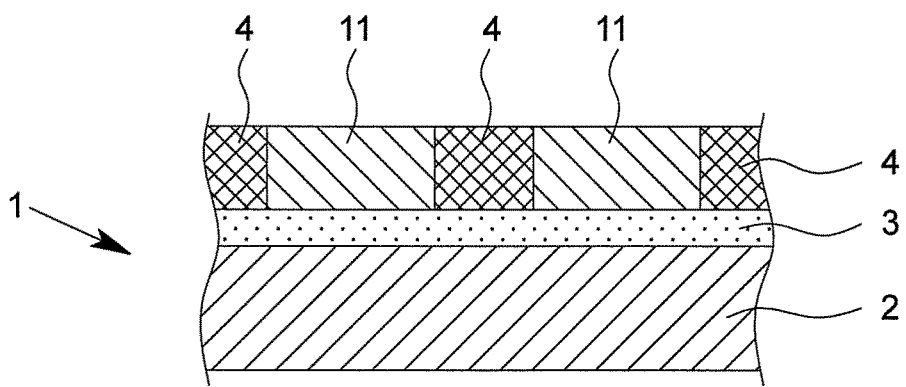
FIG. 8 is a sectional view through a chip according to the invention, wherein the coating composition is cured in some regions.

FIG. 8 shows the situation after photochemical curing with a negative photoresist. The hydrophobic coating on the chip surface 3 comprises hydrophobic regions 4 which are cured at least in part and non-cured regions 11. The non-cured regions are preferably removed by chemical means, in particular by treatment with a solvent, in particular butyric acid n-butyl ester, as a result of which the measurement regions 5 are defined and exposed.

After removal of the non-cured coating composition 11, the already photochemically cured layer 4 can be further treated thermally.

A cleaning of the chip surface by etching processes is then also conventionally carried out, in particular by the dry etching processes described above, although in this case the action time of the plasma is preferably kept so short that the hydrophobic layer 4 is not damaged. The action time of the plasma is conventionally 10 to 60 seconds, in particular 20 to 50 seconds, preferably 25 to 40 seconds, more preferably 30 seconds.

It is furthermore possible in the context of the present invention that an adhesion promoter layer (not shown in the drawing) is applied to the chip surface 3 before application of the coating composition 11. In this manner, the adhesion of the hydrophobic layer 4 to the chip surface 3 can be further improved significantly.

Individual aspects and features of the various embodiments, variants and alternatives can also be implemented independently of one another, and also in any desired combination.

What is claimed is:

1. Method for producing a plurality of measurement regions, in the form of cavities, on a chip,
   wherein:
   (a) in a first method step, a coating composition based on at least one organic polymer is applied to a chip surface of the chip, wherein the coating composition is a photoresist and wherein the coating composition is applied to the chip surface with a layer thickness in the range of from 2 to 15 μm,
   (b) in a subsequent method step, the photoresist coating composition is cured at least in part only in some regions by the application of radiation, and
   (c) in another subsequent method step, the photoresist coating composition is removed only in regions in which the photoresist coating composition has not been cured, so that individual measurement regions are fixed on the finished chip within remaining portions of the photoresist and at least one three-dimensional hydrophobic structure is formed on the chip surface bounding the measurement regions, wherein the measurement regions have a volume of from 0.2 to 500 pl.

2. Method according to claim 1, wherein the coating composition is applied to the chip surface over the complete surface thereof and wherein the removal of the coating composition in at least some regions is performed without the use of a mask.

3. Method according to claim 1, wherein the coating composition is applied to the chip surface with a layer thickness in the range of from 4 to 7 μm.

4. Method according to claim 1, wherein the coating composition is applied to the chip surface at least substantially over the complete surface.

5. Method according to claim 1, wherein the coating composition is applied to the chip surface by means of one of pouring, knife-coating, rolling, and spin-coating.

6. Method according to claim 1, wherein the coating composition is liquid with a Brookfield viscosity at 20° C. in the range of from 20 to 5,000 mPas.

7. Method according to claim 1, wherein the coating composition is liquid with a Brookfield viscosity at 20° C. in the range of from 150 to 400 mPas.

8. Method according to claim 1, wherein the coating composition is a solution or dispersion of the at least one organic polymer that comprises at least one solvent or dispersing agent selected from the group consisting of aliphatic hydrocarbons, aromatic hydrocarbons, ethers, alcohols, aldehydes, ketones and nitriles and mixtures thereof.

9. Method according to claim 1, wherein the coating composition is a solution or dispersion of the at least one organic polymer that comprises aromatic hydrocarbons.

10. Method according to claim 8, wherein the coating composition comprises the solvent or dispersing agent in amounts of from 30 to 60 wt. %, based on the coating composition.

11. Method according to claim 1, wherein the at least one organic polymer is obtainable by polymerization or oligomerization from acrylic acid, methacrylic acid, esters of acrylic acid with $C_1$- to $C_6$-alcohols, esters of methacrylic acid with $C_1$- to $C_6$-alcohols, styrene, cyclobutarenes and mixtures thereof.

12. Method according to claim 11, wherein the at least one organic polymer is obtainable from monomers of the groups of

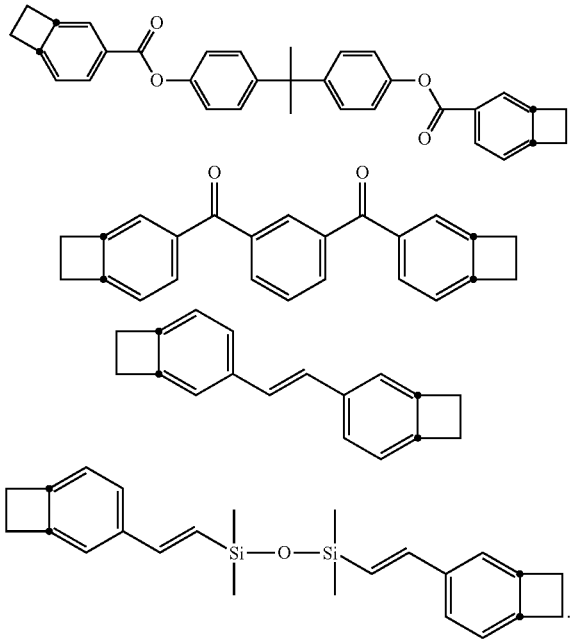

13. Method according to claim 1, wherein the at least one organic polymer has a weight-average molecular weight $M_w$ in the range of from 800 to 15,000 g/mol.

14. Method according to claim 1, wherein the at least one organic polymer has a number-average molecular weight $M_n$ in the range of from 1,000 to 100,000 g/mol.

15. Method according to claim 1, wherein the coating composition comprises the at least one organic polymer in amounts of from 25 to 55 wt. %, based on the coating composition.

16. Method according to claim 1, wherein the coating composition comprises at least one photoinitiator in an amount of from 0.01 to 10 wt. %, based on the coating composition.

17. Chip having a multiplicity of electrically addressable measurement regions formed on a surface of the chip, wherein the measurement regions are bounded by a hydrophobic structure formed of a photoresist provided fixed on the finished surface of the chip, and wherein the hydrophobic structure is formed three-dimensionally with a layer thickness of from 1 to 10 μm, and wherein the electrically addressable measurement regions have a volume of from 0.2 to 500 pl.

18. Chip according to claim 17, wherein the chip surface is formed at least substantially flat and the hydrophobic structure is raised relative to the chip surface.

19. Chip according to claim 17, wherein the hydrophobic structure separates the measurement regions from one another.

20. Chip according to claim 17, wherein the hydrophobic structure is formed in a grid-shaped and/or honeycombed pattern.

21. Chip according to claim 17, wherein the hydrophobic structure forms hydrophobic regions between the measurement regions.

22. Chip according to claim 17, wherein regions between the measurement regions have a width of more than 10%, of the diameter of a measurement region.

23. Chip according to claim 17, wherein regions between the measurement regions have a width between the measurement regions of more than 5 μm.

24. Chip according to claim 15, wherein the ratio of the height of the hydrophobic structure to the width of the hydrophobic structure in the regions between the measurement regions is at least 1:5.

25. Chip according to claim 15, wherein the ratio of the height of the hydrophobic structure to the width of the hydrophobic structure in regions between the measurement regions is in the range of from 1:5 to 1 to 1:20.

26. Chip according to claim 17, wherein the hydrophobic structure has a contact angle to water of at least 60° or more.

27. Chip according to claim 17, wherein the hydrophobic layer has a contact angle to water in the range of from 60° to 180°.

28. Chip according to claim 17, wherein the measurement regions have a diameter of from 50 to 500 μm.

* * * * *